United States Patent [19]

Dougherty et al.

[11] Patent Number: 5,021,585

[45] Date of Patent: Jun. 4, 1991

[54] AROMATIC POLYIMIDE SILANOL COMPOUNDS, PRECURSORS AND POLYMERS THEREOF

[75] Inventors: Thomas K. Dougherty, Playa Del Rey; Thomas W. Giants, Santa Monica, both of Calif.

[73] Assignee: Hughes Aircraft Company, Los Angeles, Calif.

[21] Appl. No.: 365,868

[22] Filed: Jun. 14, 1989

[51] Int. Cl.$^5$ .......................... C07F 7/18; C07F 7/10; C07B 43/06
[52] U.S. Cl. .................................. 548/406; 528/10; 556/409; 556/412
[58] Field of Search .................................. 548/406

[56] References Cited

FOREIGN PATENT DOCUMENTS 62-223228 10/1987 Japan .

*Primary Examiner*—Mark L. Berch
*Attorney, Agent, or Firm*—Mary E. Lachman; William J. Streeter; Wanda K. Denson-Low

[57] ABSTRACT

Silanol-terminated aromatic imide compounds of Formula I

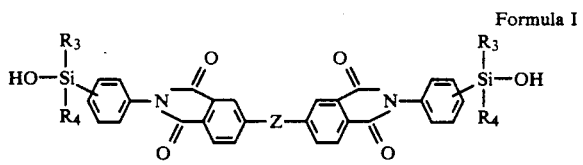

Formula I where $R_3$ and $R_4$ are each selected from the group consistsing of a $C_1$ to $C_6$ alkyl group, an unsubstituted aryl group and a substituted aryl group, Z is a divalent radical.

are prepared by: (a) reacting a bromoaniline compound with a chosen silylating agent to form a compound having the formula $BrC_6H_5NSi(R_1)_3Si(R_2)_3$, where $R_1$ and $R_2$ are each a $C_1$ to $C_4$ alkyl group
(b) reacting the compound formed in step "a" with n-butyllithium, followed by reaction with a chosen halogenated alkylsilane compound to form a compound having Formula II

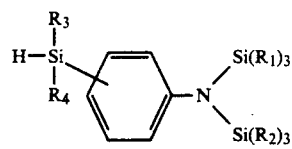

Formula II where $R_1$, $R_2$, $R_3$, and $R_4$ are as defined above
(c) reacting the compound of Formula II formed in step "b" with a dianhydride compound having the formula

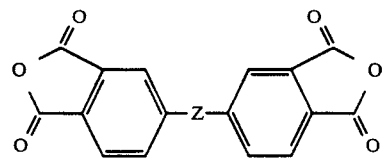

where Z is as defined above
to form a compound having Formula III

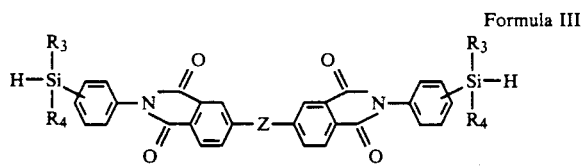

Formula III where $R_3$, $R_4$, and Z are as defined above
(d) hydrolyzing the compound of Formula III formed in step "c" to form the compound of Formula I.

The compound of Formula I may be polymerized. A preferred copolymer in accordance with the present invention is formed by polymerizing the compound of Formula I with a silicon compound having the formula

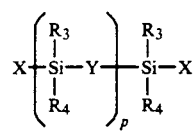

where
$R_3$ and $R_4$ are as defined above,
X=halogen, OH, OR, NRR, or ureido,
R is selected from the group consisting of a $C_1$ to $C_6$ alkyl group, an unsubstituted aryl group, and a substituted aryl groups
Y=—O— or

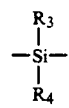

p=1 to 10.

12 Claims, No Drawings

AROMATIC POLYIMIDE SILANOL COMPOUNDS, PRECURSORS AND POLYMERS THEREOF

This invention was made with United States Government support under Contract No. F33615-86-C-5081 awarded by the Department of the Air Force. The United States Government has certain rights in this invention.

BACKGROUND OF THE INVENTION

1. Field of the Invention

The present invention relates generally to siliconcontaining compounds, methods for preparation of such compounds, and polymers thereof. More particularly, the present invention relates to silanol-terminated aromatic imide oligomers, methods for the preparation of isomers thereof, and copolymers of such oligomers with siloxane compounds. The present invention also relates to silylterminated aromatic imide compounds and silyl-protected amino silyl compounds which are useful for forming the above-noted oligomers.

2. Description of Related Art

Polyimides are widely used in the electronics and aerospace industry, for example, as coatings, adhesives, interlevel insulators in integrated circuits, and also to form composites and other structures. One such polyimide is Kapton, a trademark of E.I. duPont de Nemours, for a polymer of pyromelletic dianhydride and diaminophenylether. However, Kapton has the disadvantage that it is colored, which degrades its optical properties, and it is susceptible to atomic oxygen degradation, which makes it unsuitable for space applications in low earth orbit. One alternative to Kapton which has been used is Teflon, a trademark of E.I. duPont de Nemours for a poly (tetrafluoroethylene). While Teflon has good optical properties, it suffers from the serious problem of poor adhesion. Yet another alternative material that has been used is silicone. However, despite the good optical properties and good atomic oxygen resistance of silicones, they are impractical because of their poor mechanical properties. Finally, siloxane-polyimides have been developed as described, for example, by Policastro et al, in the publication "Siloxane Polyimides for Interlevel Dielectric Applications," in the *Proceedings of the ACS Division of Polymeric Materials: Science and Engineering*, Vol. 59, 1988, Los Angeles, California, pages 209-213. However, such polymers are colored, and contain the weak links of the polyalkylene group, which degrades the thermooxidative properties of the polymer.

Thus, a need presently exists for a polymer which has in combination, good optical properties, good thermooxidative stability, resistance to atomic oxygen degradation, good mechanical properties, and good processing characteristics.

SUMMARY OF THE INVENTION

The general purpose of the present invention is to provide new silanol-terminated aromatic imide oligomers from which new poly(imide-siloxane) polymers and other polymers may be prepared. These polymers possess most, if not all, of the advantages of the above-mentioned prior art polymers while overcoming their above-noted significant disadvantages.

The above-described general purpose of the present invention is accomplished by first preparing a silanol-terminated aromatic imide compound having Formula I below.

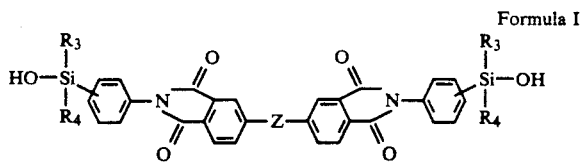

Formula I where $R_3$ and $R_4$ are each selected from the group consisting of a $C_1$ to $C_6$ alkyl group, an unsubstituted aryl group and a substituted aryl group, Z is a divalent radical.

The compound of Formula I is prepared by:

(a) reacting a bromoaniline compound with a chosen silylating agent to form a compound having the formula

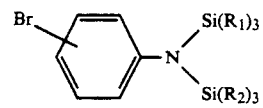

where $R_1$ and $R_2$ are each a $C_1$ to $C_4$ alkyl group or where the group $-NSi(R_1)_3Si(R_2)_3$ is 2,2,5,5-tetramethyl-1-aza-2,5-disilacyclopentane.

(b) reacting the compound formed in step "a" with n-butyllithium, followed by reaction with a chosen halogenated alkylsilane compound to form a compound having Formula II

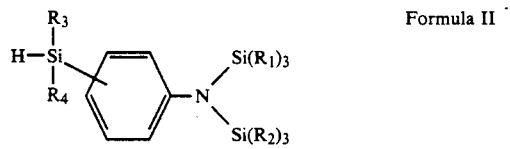

Formula II where $R_1$, $R_2$, $R_3$, and $R_4$ are as defined above.

(c) reacting the compound of Formula II formed in step "b" with a dianhydride compound having the formula

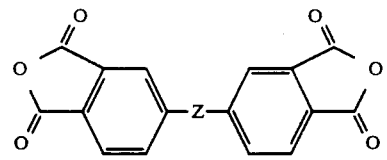

where Z is a divalent radical
to form a compound having Formula III

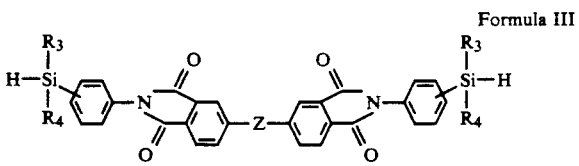

Formula III where $R_3$, $R_4$, and Z are as defined above.

(d) hydrolyzing the compound of Formula III formed in step "c" to form the compound of Formula I.

The compound of Formula I may be homopolymerized or it may be copolymerized, for example with silanol compounds, or other compounds which react with the silanol group of Formula I. A preferred copolymer in accordance with the present invention is formed by polymerizing the compound of Formula I with a silicon compound having the formula

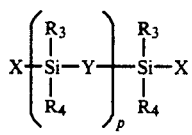

where $R_3$ and $R_4$ are as defined above,
X=halogen, OH, OR, NRR, or ureido,
Y=—O—or

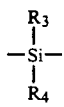

p=1 to 10

These copolymers have been found to be resistant to erosion by oxygen plasma.

DESCRIPTION OF THE PREFERRED EMBODIMENT

The silanol-terminated aromatic imide oligomers of the present invention are represented by Formula I below, which indicates attachment of the silicon-containing radical to the aromatic ring in either the ortho, meta, or para position. The meta and para isomers are preferred.

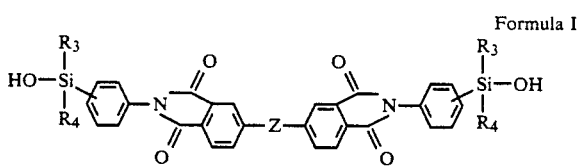

Formula I where $R_3$ and $R_4$ are each selected from the group consisting of a $C_1$ to $C_6$ alkyl group, an unsubstituted aryl group and a substituted aryl group, Z is a divalent radical.

The synthesis of the compound of Formula I is achieved in accordance with the present invention by means of the compounds of Formula II and III below, which are also novel compounds in accordance with the present invention.

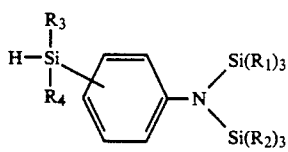

Formula II where $R_1$ and $R_2$ are each a $C_1$ to $C_4$ alkyl group or where the group -NSi($R_1$)$_3$Si($R_2$)$_3$ is 2,2,5,5-tetramethyl-1-aza-2,5-disilacyclopentane. $R_3$ and $R_4$ are as defined above.

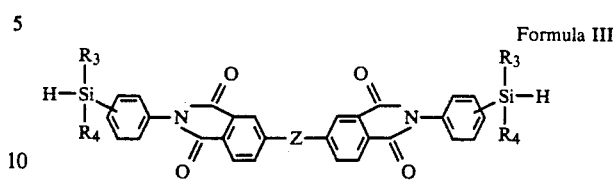

Formula III where $R_3$, $R_4$ and Z are as defined above.

The sequence of reactions for forming the compound of Formula I is essentially the same for the meta and para isomers. However, the chemical processes used to achieve this reaction sequence are different for the two isomers, as discussed in further detail below.

Synthesis of the compound of Formula I begins by reacting bromoaniline (Compound 1) with a silylating agent, to form the corresponding silylated bromoaniline compound (Compound 2), in which the nitrogen atom of the amine group is protected by alkylsilyl groups.

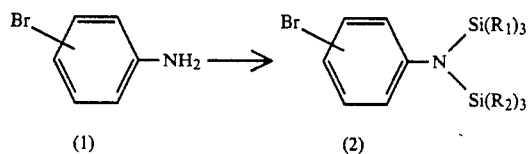

where $R_1$ and $R_2$ are each a $C_1$-$C_4$ alkyl group or where the group -NSi($R_1$)$_3$Si($R_2$)$_3$ is 2,2,5,5-tetramethyl-1-aza-2,5-disilacyclopentane.

Next, the bromine in Compound 2 is replaced by a silanecontaining group by reaction with a silylating agent, to form Compound 3, which corresponds to Formula II above.

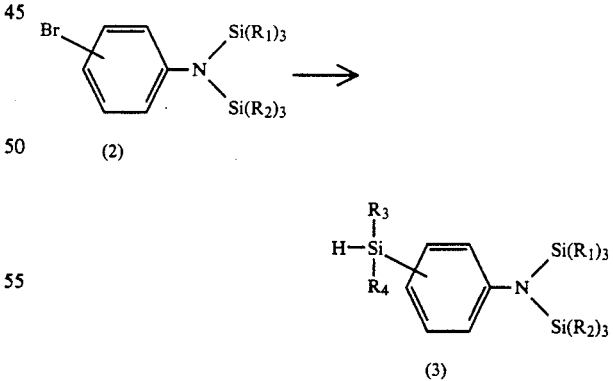

where $R_1$ and $R_2$ are as defined above; $R_3$ and $R_4$ are each a $C_1$ to $C_6$ alkyl group, an unsubstituted aryl group or a substituted aryl group.

Then, Compound 3 is reacted with a dianhydride compound (Compound 4) to form the disilyl terminated imide oligomer (Compound 5), which corresponds to Formula III above.

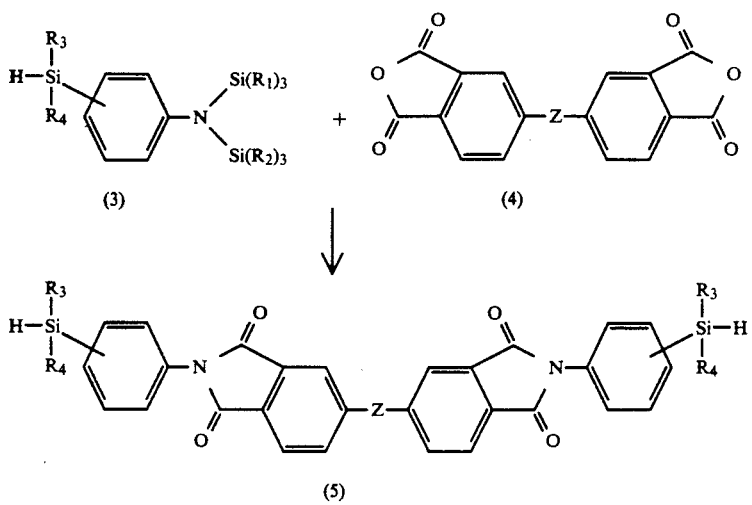

where $R_1$, $R_2$, $R_3$, $R_4$ and Z are as defined above;
With regard to Compounds 4 and 5, Z is defined as a divalent radical. Preferred radicals for Z are $-C(CF_3)_2-$, CO, $SO_2$, O, or a diamine-dianhydride adduct. The latter term is intended to mean an anhydride end-capped imide obtained by reacting a diamine with an excess of dianhydride. For example, Compound 4 may be reacted with a diamine as shown below.

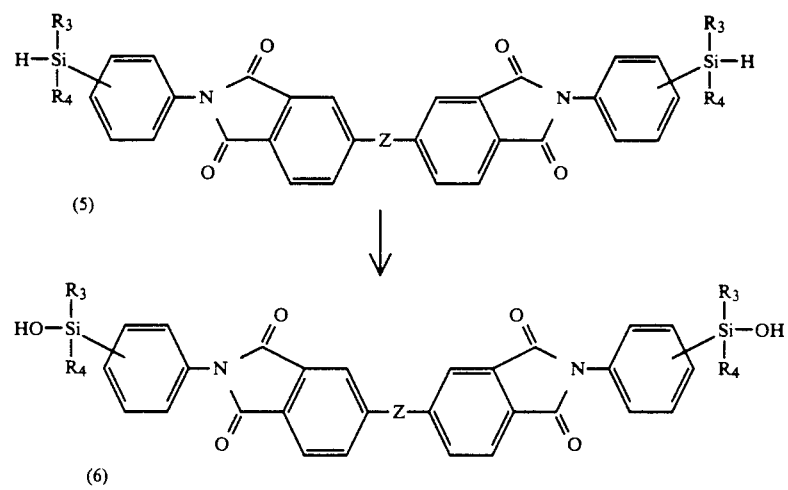

where $R_3$, $R_4$, and Z are as defined above

Turning now to more specific detail of the reaction sequence indicated above, preparation of the meta isomer of Formula I will be discussed first and followed by a discussion of the preparation of the para isomer of Formula I. For the preparation of the meta isomer of

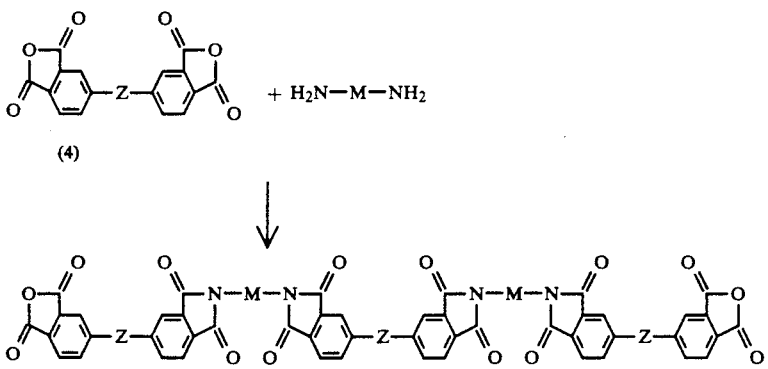

where Z is as defined above, and M is a divalent radical
As noted, M is a divalent radical, such as phenylene or alkylene, for example, ethylene. Finally, the disilyl terminated Compound 5 is hydrolyzed to the disilanol terminated imide oligomer (Compound 6), which corresponds to Formula I above.

Formula I, in the above-noted conversion of Compound 1 to Compound 2, the starting material (Compound 1) is 3-bromoaniline and the silylating agent is a disilane compound such as 1,1,4,4-tetramethyl-1,4-bis(N,N-diethylamino)-1,4disilabutane. Other silyating agents which may be used include, but are not limited to, chlorotrimethylsilane, any trialkyl chlorosilane, or any triaryl chlorosilane. Next, in the conversion of the meta isomer of Compound 2 to the meta isomer of Compound 3 (or Formula II), silylation is accomplished by reacting the meta isomer of Compound 2 with n-butyllithium, followed by reaction with a halogenated silane compound, such as chlorodimethylsilane. This method for forming the compound of Formula II is considered to be new in the art. Then, the meta isomer of Compound 3 is added in excess to a dianhydride, such as 4,4'-(hexafluoroisopropylidene)bisphthalic anhydride, and refluxed to form the meta isomer of Compound 5 (or Formula III). This method of forming the imide compound of Formula III is considered to be new in the art since the alkylsilyl groups protecting the nitrogen in Compound 3 are not removed prior to reaction with the dianhydride (Compound 4) and this transformation is carried out in the presence of the silane (Si-H) group. Finally, the disilane Compound 5 (meta isomer) is hydrolyzed in a pH 7 phosphate buffer solution in the presence of 5 percent palladium on carbon, to form the meta isomer of Compound 6. In general, the meta isomers of the compounds of Formula I are easier to synthesize and handle than the para isomers, since Compound 3 (meta) is more reactive for forming Compound 5, and Compound 6 (meta) is more stable and easier to purify as compared to the para isomer.

For the preparation of the para isomer of Formula I, in the above-noted conversion of the para isomer of Compound 1 to the para isomer of Compound 2, the starting material (Compound 1) is 4-bromoaniline and the silylation is accomplished by first reacting Compound 1 with n-butyllithium, followed by reaction with a halogenated silane compound, such as chlorotrimethylsilane. Next, in the conversion of the para isomer of Compound 2 to the para isomer of Compound 3 (or Formula II), silylation is accomplished by reacting the para isomer of Compound 2 with n-butyllithium, followed by reaction with a halogenated silane compound, such as chlorodimethylsilane. This method for forming the compound of Formula II is considered to be new in the art. Then, the Para isomer of Compound 3 is dissolved in a chosen dianhydride, such as 4,4'-(hexafluoroisopropylidene)bisphthalic anhydride, and refluxed to form the para isomer of Compound 5 (or Formula III). As noted above, this method of forming the imide compound of Formula III is considered to be new in the art since the protective alkylsilyl groups in Compound 3 are not removed prior to reaction with the dianhydride compound and this transformation is carried out in the presence of the silane (Si—H) group. Finally, the disilane Compound 5 (para isomer) is hydrolyzed in a pH 7 phosphate buffer solution in the presence of 5 percent palladium on carbon, to form the para isomer of Compound 6.

The compounds of Formula I are useful for forming polymers and copolymers. One particularly useful copolymer is formed by reacting the para isomer of the compound of Formula I with a siloxane compound (7) to form a poly(imide-siloxane) polymer of Formula IV, where the silicon atom is attached to the aromatic ring in the para position and Y is oxygen.

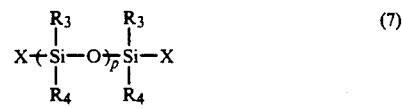

where X=halogen, OH, OR, NRR, or ureido
R=a $C_1$ to $C_6$ alkyl group, an unsubstituted aryl group, or a substituted aryl group
$R_3$ and $R_4$=a $C_1$-$C_6$ alkyl group, an unsubstituted aryl group, or a substituted aryl group
p=1−10

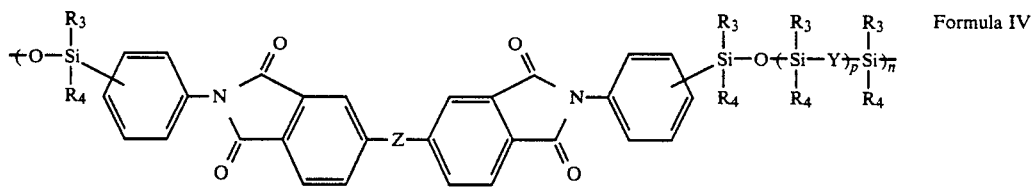

Formula IV where $R_3$, $R_4$, Z, and p are as defined above
Y=—O—or

n=1 to about 1000

The polymer of Formula IV where the silicon atom is attached to the aromatic ring in the meta position and Y is —$SiR_3R_4$—, is formed by reacting the meta isomer of the compound of Formula I with a silane compound (8)

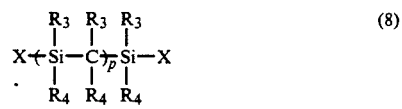

where $R_3$, $R_4$, X, and p are as defined above.

Compounds (7) and (8) may be represented by the generic formula

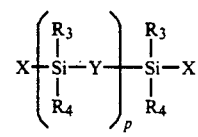

where
$R_3$, $R_4$, X, and p are as defined above
Y=—O—or

The block copolymer of Formula IV is formed by known methods such as described by Merker et al in the publication entitled "Random and Block Copolymers of Poly(tetramethyl-p-Silphenylene-Siloxane) and Polydimethylsiloxane" in the *Journal of Polymer Science*, Path A, Vol. 2, 1964, pages 31-44. The copolymer of Formula IV possesses the best properties of both imide polymers and siloxane polymers. The aromatic imide linkage enhances the thermal and mechanical properties of the structures; and the siloxane moiety greatly improves the processability of the structure. In addition, by eliminating the polyalkylene linkage which is found in known polyimidesiloxanes, the copolymers of Formula IV have improved thermo-oxidative stability. Furthermore, the copolymers of Formula IV have high optical transmission (i.e., are colorless), which is essential for high efficiency of solar cells. These copolymers also have good resistance to atomic oxygen and ultraviolet radiation, which is necessary for space applications in low earth orbit, as described in Example 5.

The compounds of Formula I may also be homopolymerized using known methods for polymerizing silanol compounds, such as described by Merker et al in the publication entitled "Random and Block Copolymers of Poly(tetra-methyl-p-Silphenylene-Siloxane) and Polydimethyl- siloxane" referenced above. The homopolymers of the compound of Formula I have a large amount of imide per siloxane group which makes them useful materials where high melting point, good solvent resistance, and excellent mechanical properties (tensile strength) are needed.

In addition to their usefulness in synthesizing the compounds of Formula I, the new compounds of Formula II in accordance with the present invention may be used as a substituted amine and, for example, may be reacted with water to form the corresponding amine. The new compounds of Formula III may alternatively be used for forming imide-silane compounds and polymers, such as by an addition reaction with a compound containing a vinyl or other unsaturated group. The latter compounds are useful for crosslinking agents in room temperature vulcanization (RTV) systems and other applications.

Examples of practice of the present invention are described below. The following general procedure was used for all examples.

General Explanation of Examples

All reactions were carried out under a dry nitrogen atmosphere using standard synthetic methodology. The air sensitive reactions were performed using apparatus described by Shriver and Dreizden in the book entitled "Manipulation of Air Sensitive Compounds," Wiley & Sons, 1986. Gel permeation chromatograms were taken using a Waters chromatography system with Styragel columns standardized with polystyrene standards. Proton NMR spectra were recorded at 200 MHz on a Bruker AC200, spectrometer. The residual protons in the CDCl$_3$ solvent were used as reference of 7.27 ppm because of the complication of adding an extra silicon peak of tetramethylsilane in the NMR spectra. The Carbon-13 NMR spectra were recorded at 50.323 MHz on the same instrument. These spectra were referenced to the carbon peak of the solvent CDCl$_3$ IR spectra of liquids and polymers were taken of thin films on NaCl plates. IR spectra of solids were observed in KBr emulsions. All IR spectra were recorded on a Nicolet MX-1 Fourier transform NMR spectrometer. Thermal analyses were performed on a Dupont 951 TGA and 910 DSC with a 1090 data acquisition station.

EXAMPLE 1

This example describes the series of process steps used for the synthesis of the compound of Formula I where $R_3=R_4=-CH_3$, $Z=-C(CF_3)_2-$, and the silicon atom is attached to the aromatic ring in the para position.

A. Preparation of N,N-Bis(trimethylsilyl)-4-bromoaniline.

The general procedure described by J.R. Pratt et al, in the publication entitled "Organosilicon Compounds. XX. Synthesis of Aromatic Diamines via Trimethylsilyl-Protecting Aniline Intermediates," *J. Org. Chem.*, Vol. 40, No. 8, 1975, pages 1090 to 1094, was followed with some modifications as described herein. To a tetrahydrofuran (500 ml) solution of p-bromoaniline (106.0g, 0.62 mol) cooled to 0° C. there was added over a period of one hour n-butyllithium (825 ml, 1.3 mol). The reaction mixture turned brown but remained homogeneous. The reaction mixture was refluxed for 2 hours to complete the metallation, cooled to ice temperature, and then chlorotrimethylsilane (180 ml, 1.4 mol) was added so as to not let the reaction temperature exceed 15° C. The reaction mixture was allowed to warm to room temperature and was refluxed overnight. Filtration was accomplished by the Schlenk technique, and a gas chromatogram (GC) was taken. The solvent was evaporated and the residue was distilled to give three fractions: Fraction 1 - b.p. 25°-89° C./0.5 torr, 22.0g (this forerun was discarded); Fraction 2 - b.p. 90°-108° C./0.5 torr, 32g, 95% pure by GC (the impurity being the mono-TMS adduct); and Fraction 3 -b.p. 108°-109° C./0.5 torr, 122.4g, 99% pure by GC; product Fractions 2 and 3 amounted to a 79% yield. IR (NaCl plates); 2940, 1470, 1250, 1220, 940, 900, 860; Hl NMR (CDCl$_3$) 7.9 (dd, AA'MM, 4H), 0.5 (s, 18H).

B. Preparation of N,N-Bis(trimethylsilyl)-4-dimethylsilylaniline.

To the compound prepared in Step "A" above (15.8g, 0.052 mol) in ether (140 ml) at 0° C. there was added n-butyllithium (26 ml of a 2.1 M solution in hexane, 0.055 mole). The reaction mixture was stirred at this temperature for 1 hour. A small aliquot was removed and worked up in water. GC analysis of this sample showed that the metallation was complete. The contents of the reaction flask were transferred using the double needle technique to dimethylchlorosilane (6.0 ml) in ether (40 ml), all at 0° C. The reaction mixture was allowed to warm to room temperature and stirred overnight. The reaction mixture was then diluted with an equal volume of hexane, filtered using the Schlenk apparatus, and the solvent was evaporated. The residue was analyzed by GC and NMR and distilled to give a fraction boiling at 92°-96° C./0.4 torr (12.2g, 80%). Hl NMR (CDCl$_3$); 7.6 (dd, AA'MM', 4H), 4.8 (septet, lH), 0.85 (d, 6H), 0.5 (s, 18H). 13 C-NMR (CDCl$_3$) 149.12, 134.28, 131.44, 129.72, 2.15, −3.58.

C. Preparation of N,N'-Bis[4-(dimethylsilyl)phenyl]-4,4'-[2,2,2-trifluoro-1-(trifluoromethyl)ethylidene]-bisphthalimide.

The bis-trimethylsilyl-protected silylamine prepared in Step "B" above (5.0g, 0.017 mole) was dissolved with hexafluoro-isopropylidene-4,4'bisphthalic anhydride (6F-dianhydride) (3.31g, 0.007 mole) in N-methylpyrrolidinone (NMP) (10 ml) and toluene (40 ml). The reaction mixture was refluxed with a Dean-Stark trap for 12 hours and cooled overnight. GC analysis through a 3-meter capillary column was used to monitor the reaction. The next day the reaction mixture was poured into water (100 ml), extracted with methylene chloride (100 ml), and dried over $Na_2SO_4$. The solution was evaporated and triturated (50 ml of a 1:1 methanol/water mixture). The resulting solid (3.2g, 62%) did not melt below 270° C. but was very soluble, and the propose d structure was confirmed by IR and NMR analysis. IR (KBr); 2970, 2120, 1780, 1720, 1370, 1250, 1220, 1190, 1150, 1100, 870, 720. H1 NMR (DMSO-$d_6$); 9.0-8.0 (m, 14H), 5.0 (septet, 2H), 0.85 (d, 12H).

D. Preparation of N,N'-Bis[4-(dimethylhydroxysilyl)phenyl]-4,4'-[2,2,2-trifluoro-1-(trifluoromethyl)ethylidene]bisphthalimide.

To the 6F-diimidedisilane prepared in Step "C" above (15.0g, 0.021 mol) in THF (80 ml) there was added an aqueous pH 7 buffer (16 ml, phosphate type) and palladium on carbon (100 mg of 5% metal). The reaction was followed by thin layer chromatography (TLC) (2 to 1 methylene chloride/THF; Rf disilane=0.7; Rf disilanol=0.2). The reaction was stirred overnight and appeared complete. Great care must be taken at this stage to prevent self condensation of the disilanol Product. The disilanol was isolated by filtration and dried over $Na_2SO_4$. The resulting yellow solution was concentrated to about 30 ml without heating and then immediately columned on silica gel (first fraction in 100% $CHCl_3$ eluent, product fraction from 5% THF in $CHCl_3$). The resulting fractions were analyzed by TLC and the product fractions were carefully concentrated without heating. The residue was triturated with toluene to give a pale yellow solid (7.0g, 44%). IR (neat); 3500 brd, 2950, 1740, 1770, 1375, 1270, 860, 840. H1-NMR; 8.03, (d, 2H), 7.91 (s, 2H), 7.99 (d, 2H), 7.74 (d, 4H), 7.42 (d, 4H), 1.95 (brd s, 2H), 0.42 (s, 12 H); 13 C NMR 166.03, 165.89, 139.95, 139.15, 135.88, 134.02, 132.62, 132.31, 126.21, 125.72 (2 Carbons), 125.39, 124.16, 123.34, (quartet, J(C,F) =287 Hz), 64.15 (septet, J(C,F) =26 Hz), 0.02.

EXAMPLE 2

This example describes the series of process steps used for the synthesis of the compound of Formula I where $R_3=R_4=-CH_3$, $Z=-C(CF_3)_2-$, and the silicon atom is attached to the aromatic ring in the meta position.

A. Preparation of 1-(3-bromophenyl)-2,2,5,5-tetramethyl-1-aza-2,5-disilacyclopentane.

3-bromoaniline (77g, 0.45 mol) was added to an excess (150g) of 1,1,4,4-tetramethyl-1,4-bis(N,N-diethylamino)-1,4-disilabutane. The latter may be formed by the method of T. L. Guggenheim as described in the publication entitled "Protection of Substituted Anilines with 1,1,4,4-Tetra-methyl-1,4-Bis-(N,N-Dimethylamino) Disilethylene," Tetrahedron Letters, Vol. 25, No. 12, 1984, pages 1253 to 1254. The reaction mixture was heated to 190° C. over 8 hours and allowed to stir at that temperature overnight. Distillation of the reaction mixture gave the product as a colorless liquid (109.3g, 70% of theoretical, b.p. 94°-98° C., 0.25 torr). This compound was taken on to the next reaction (Step B) without further characterization.

B. Preparation of 1-(3-(dimethylsilyl)phenyl)-2,2,5,5-tetramethyl-1-aza-2,5-disilacylopentane.

The protected bromoaniline prepared in Step "A" above (15g, 0.048 mol) was dissolved in diethylether (125 ml) and cooled to 0° C. n-Butyllithium in hexane (30 ml, 0.063 mol) was added to this solution over 30 minutes. The reaction was allowed to stir an additional 30 minutes and then the metallated protected aniline reaction mixture was added by the double needle technique to chlorodimethylsilane (9 ml, 0.08 mol) in ether (50 ml) at 0° C. The reaction was allowed to warm to room temperature and was then filtered by the Schlenk technique to give a clear yellow solution. Concentration and distillation of this mixture gave a fraction boiling at 92°-94° C./0.25 torr (8.4g, 62% of theory), H1 NMR ($CDCl_3$) 7.4-7.0 (m, 4H), 4.55 (m, 1H), 1.00 (m, 4H), 0.48 (m, 6H), 0.37 (m, 12H); C13 NMR ($CDCl_3$) 146.88, 137.83, 128.71, 128.56, 125.67, 123.96, 8.46, 0.06, −3.77; Si 29 NMR ($CDCl_3$) 13.49, −17.22; IR (neat) 2954, 2916, 2889, 2118, 1581, 1562, 1250, 910, 789, 760.

C. Preparation of N,N'-Bis(3-dimethylsilyl)phenyl-4,4'-(hexafluoroisopropylidene)bisphthalimide.

An excess of the protected dimethylsilane aniline prepared in Step "B" above (5.0g) was added to 4,4'-(hexafluoroisopropylidene)bisphthalic anhydride (3.02g, 0.068 mol) in toluene (50 ml). The reaction was refluxed for 20 hours using a Dean Stark trap. The reaction mixture was concentrated and the crude product was subjected to flash column chromatography (silica gel, dichloro-methane/hexane eluent). The light yellow solid weighed 2.21g (45% of theory). H1 NMR $CDCl_3$) 8.10-7.95 (m, 6 H), 7.67-7.39 (m, 8H), 4.57 (septet, 2H, J=3.8 Hz), 0.42 (d, 12H, J=3.8 Hz); C13 NMR ($CDCl_3$) (H1 decoupled) 165.93, 165.75, 139.00, 138.86, 135.70, 133.89, 132.54, 132.26, 131.72, 130.85, 128.57, 127.18, 125.09, 123.89, 128.95 (quartet, J(C,F)=286.8), 66.20 (septet, J =26.2 Hz), −4.17; Si-29 NMR (CDCl3) −16.41; IR (KBr) 2942, 2122, 1782, 1720, 1369, 1253, 1111, 895, 721.

D. Preparation of N,N'-Bis(3-hydroxydimethysilyl)-phenyl-4,4'-(hexafluoroisopropylidene)bisphthalimide.

The diimidedisilane prepared in Step "C" above (2.0g, 0.0028 mol) was dissolved in THF (20 ml). To this there was added a pH 7 phosphate buffer solution (10 ml) and 5% palladium on carbon (150 mg). The reaction was stirred for 6 hours. TLC analysis of the reaction mixture (silica gel/chloroform - THF eluent) showed hydrolysis to be complete. The reaction mixture was filtered through celite, taken up in ether, washed with saturated NaCl and dried over $Na_2O_4$. Concentration of the dried ethereal solution gave 1.4g (68% of theory) of a light yellow solid. IR (KBr) 3500 (brd), 2945, 1782, 1720, 1373, 1254, 892, 721; H1 NMR ($CDCl_3$) 8.12-7.83 (m, 6H), 7.66-7.32 (m, 8H), 0.44 (s, 12H). C13 NMR ($CDCl_3$) 166.18, 166.07, 141.25, 139.08, 135.87, 133.19, 132.33, 132.33, 131.04, 130.80, 128.75, 127.57, 126.19 (q, J(C,F) =287.3 Hz), 125.26, 124.06, 67.81 (m), -0.15; Si29 NMR ($CDCl_3$) −6.744.

EXAMPLE 3

This example describes the preparation of the copolymer of Formula IV where $R_3$ and $R_4$ each= $-CH_3$, $Z=-C(CF_3)_2-$, the silicon atom is attached to the aromatic ring in the para portion, and Y is oxygen.

The 6F-diimidedisilanol monomer prepared in Example 1, step "D" above (3.826g, 0.00526 mol) was dried (50° C./0.05 torr) overnight and then placed in the dry box. The monomer was dissolved in chlorobenzene (10 ml) with magnetic stirring. The reaction mixture was slowly stirred at room temperature during the slow addition of tetramethylbisureidosiloxane (12.5 ml of a stock solution analyzed by NMR, 0.00515 mol) over 20 hours. The next day, the reaction solution was analyzed by NMR (neat/no lock solvent) and found to contain a slight excess of the ureido moiety. The silanol monomer of the present invention (50 mgs) was added in two equal portions over 24 hours, and the reaction was worked up by removal from the box and precipitating the chlorobenzene solution in methanol and precipitated once more into methanol (100 ml). The yellow polymer was filtered, taken up in methylene chloride (25 ml) and precipitated once more into methanol (200 ml). The yellow solid weighed 1.9g (48%). IR (thin film); 2950, 1740, 1340, 1260, 1175, 1080, 800; H1 NMR (CDCl$_3$) 8.00 (d, 2H, J = 7.7 Hz), 7.92 (s, 2H), 7.84 (d, 2H, J=7.7 Hz), 7.69, (d, 4H, J=8.3 Hz), 7.39 (d, 4H, J=8.3 Hz), 0.34 (s, 12H), 0.072 (s, 12H). Tg (DSC) 130° C. visc.=0.291. Weight average molecular weight/weight average molecular number or Mw/Mn (GPC) 42,000/26,000.

EXAMPLE 4

This example describes the preparation of the copolymer of Formula IV where $R_3$ and $R_4$ each=—CH$_3$, Z=—C(CF$_3$)$_2$-, the silicon atom is attached to the aromatic ring in the meta position, and Y is a single bond.

The 6F-diimidedisilanol monomer prepared in Example 2, Step "D" above (2.0g, 0.0027 mol), was dissolved in chlorobenzene (15 ml) in a dry box. To this there was added in two portions dimethylbisureidosilane (1.2g, 0.0027 mol, formed by the method of Hedaya et al described in the publication entitled "D$_2$-meta-Carborane-Siloxanes. IV. Synthesis of Linear, High Molecular Weight Polymers," in the *Journal of Polymer Science*; Polymer Chemistry Edition, Vol. 15, 1977, pages 2229-2238. The reaction was allowed to stir for 2 hours, then a small aliquot was removed and analyzed by NMR. The NMR revealed no ureido monomer, therefore an additional small amount (150 mg) of the dimethylbisureido monomer was added. The reaction mixture was stirred for one hour. An NMR showed excess ureido, and the disilanol (80 mg) was added. The reaction mixture was stirred for one hour. An NMR of this mixture showed no ureido. The reaction mixture was then back-titrated with the ureido monomer (100 mg, 14 hours, syringe pump). The next day the reaction mixture was removed from the box, precipitated into methanol, washed with methanol, dissolved in chloroform, again precipitated into methanol and dried (60° C., 8 hours) to give a light yellow solid (1.8g, 83% of theory). GPC 88,000/41,000; UV-VIS(1,2- dichloroethane) 50% cutoff at 380 nm, IR (KBr) 2957, 1782, 1724, 1373, 1368, 1256, 1044, 795; H1 NMR (CDCl$_3$) 8.03–7.83 (m, 6H), 7.64–7.34 (m, 8H), 0.32 (s, 12H), 0.07 (s, 6H). C13 NMR (CDCl$_3$) 166.18, 166.00, 141.48, 139.08, 135.85, 133.16, 132.71, 132.41, 130.91, 130.77, 128.66, 126.24, 125.10 (q, J(C,F)=287.3 Hz), 125.29, 124.06, 67.81 (m), 0.65, −1.28; Si29 NMR (CDCl$_3$) −2.42, −18.55.

EXAMPLE 5

This example describes the testing of the copolymer formed in Example 3 to determine its resistance to erosion by an oxygen plasma, including elemental oxygen. Four specimens for testing were prepared by forming a layer of the copolymer of Example 3 on each of four graphite/epoxy substrates having dimensions of 1 inch (2.54 cm) by 2 inches (5.08 cm) by 0.310 to 0.370 inch (0.787 to 0.940 cm) and obtained from U.S. Polymeric, E42-1/GY70. The coating thickness was 0.0016 inch (0.004 cm). The substrates were coated by solvent casting. Mass and optical measurements of each specimen were made before plasma exposure by the same methods described below for the measurements after exposure.

The specimens were placed two at a time in a Plasma Prep II Plasma Asher. In order to assure that the plasma was consistent during each exposure, a piece of Kapton was included with each sample pair. If the Kapton erosion yield from the first exposure was consistent with that from the second exposure, it could be assumed that the plasma environment was consistent for both pairs. The Kapton erosion yield from both exposures was used to determine an equivalent atomic oxygen fluence level in low earth orbit. The samples were exposed to atomic oxygen for seventy two hours in the asher, which corresponds to an equivalent fluence of $5 \times 10^{20}$ at/cm$^2$. The pressure in the asher was approximately 25 micrometers.

The samples were left under vacuum for forty-eight hours prior to plasma exposure in order to increase the accuracy of the Kapton sample mass measurement through dehydration. Samples were weighed after dehydration on a balance accurate to $10^{-5}$ g. After exposure, the samples were removed from the asher and quickly weighed to determine mass loss of the sample after ashing. Final optical characterization was performed with the Perkin Elmer Lambda 9 UV/VIS/NIR spectrophotometer to determine the reflectance and transmittance after exposure to atomic oxygen in the Plasma Prep II Plasma Asher.

The test results for mass loss are shown in Table I below. As can be seen, the specimens had essentially no mass loss after exposure to the oxygen plasma. These results indicate the suitability of these copolymers of the present invention for providing protective coatings and structures that are resistant to erosion by oxygen plasma, such as that encountered in external low earth orbit. It was, however, noted that these specimens experienced a change in specular solar transmittance after exposure to the oxygen plasma which degraded their optical performance and which would make them unsuitable for optical coatings.

TABLE I

| | PLASMA EROSION RESULTS | |
|---|---|---|
| Specimen No. | Mass Before Ashing (g) | Mass After Ashing (g) |
| 1 | 12.00341 | 12.00336 |
| 2 | 12.00348 | 12.00382 |
| 3 | 12.00337 | 12.00379 |
| 4 | 12.00350 | 12.00391 |

Other copolymers of the present invention having Formula IV, where $R_3$, $R_4$, Z, and Y are other groups as specified previously herein, are expected to exhibit similar resistance to erosion by an oxygen plasma as the particular copolymer specified in this example.

EXAMPLE 6

Preparation of Poly(N,N'-(dimethylsilyoxy-dimethylsilylphenyl-4,4'-(hexafluoroisopropylidene)bisphthalimide.

This example illustrates one method of preparing homopolymers of the compounds of Formula I.

The disilanol prepared in Example 2 (5.0g, 0.0067 mole) was dissolved in dry toluene (20 ml) in a round bottom flask (100 ml). To this solution there was added the catalyst n-hexylamine-2-ethylhexoate. The reaction was refluxed 24 hours and worked up by pouring into methanol (200 ml) and drying in vacuo. The polymer weighed 4.2g (88%) and had NMR and IR consistent with the structure. GPC (Mw/Mn) (46,000/29,000).

Having thus described exemplary embodiments of the present invention, it should be noted by those skilled in the art that the disclosures within are exemplary only and that various other alternatives, adaptations and modifications may be made within the scope of the present invention. Accordingly, the present invention is not limited to the specific embodiments as illustrated herein, but is only limited by the following claims.

What is claimed is:

1. A compound having Formula I

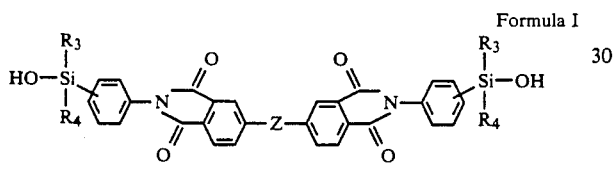

Formula I where $R_3$ and $R_4$ are each selected from the group consisting of a $C_1$ to $C_6$ alkyl group and an aryl group, and Z is a divalent radical selected from the group consisting of —$C(CF_3)_2$—, CO, $SO_2$, and O.

2. The compound of claim 1 wherein:
   (a) the silicon-containing radical is attached to the aromatic ring in the para position;
   (b) $R_3$ and $R_4$ are each methyl; and
   (c) Z is —$C(CF_3)_2$—.

3. The compound of claim 1 wherein:
   (a) the silicon-containing radical is attached to the aromatic ring in the meta position;
   (b) $R_3$ and $R_4$ are each methyl; and
   (c) Z is —$C(CF_3)_2$—.

4. A method for forming a compound having Formula I

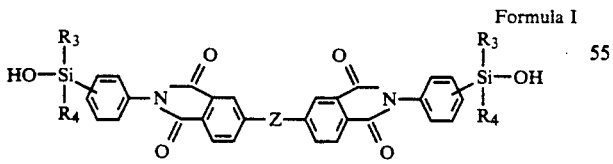

Formula I where $R_3$ and $R_4$ are each selected from the group consisting of a $C_1$ to $C_6$ alkyl group and an aryl group, and Z is a divalent radical selected from the group consisting of —$C(CF_3)_2$—, CO, $SO_2$, and O comprising the steps of:

(a) reacting a bromoaniline compound with a chosen silylating agent to form a compound having the formula

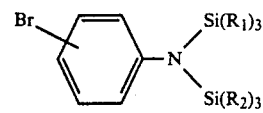

where $R_1$ and $R_2$ are each a $C_1$ to $C_4$ alkyl group or where the group —$NSi(R_1)_3Si(R_2)_3$ is 2,2,5,5-tetramethyl-1-aza2,5-disilacyclopentane (b) reacting the compound formed in step "a" with n-butyllithium, followed by reaction with a chosen halogenated silane compound to form a compound having Formula II

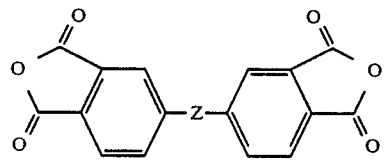

Formula II where $R_1$, $R_2$, $R_3$, and $R_4$ are as defined above (c) reacting the compound of Formula II formed in step "b" with a dianhydride compound having the formula

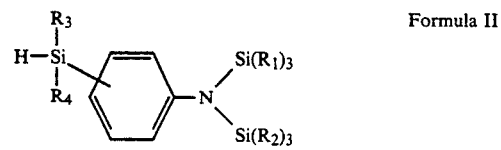

where Z is as defined above to form a compound having Formula III

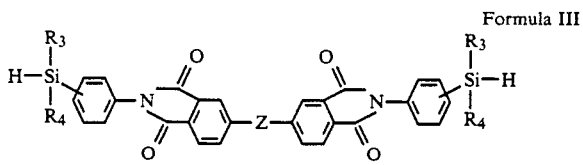

Formula III where $R_3$, $R_4$, and Z are as defined above (d) hydrolyzing the compound of Formula III formed in step "c" to form the compound of Formula I.

5. The method of claim 4 wherein:
   (1) in Formula I, the silicon-containing radical is attached to the aromatic ring in the meta position;
   (2) in step "a" said chosen silylating agent comprises 1,1,4,4-tetramethyl-1,4-bis(N,N-diethylamino)-1,4-disilabutane; and
   (3) in step "b" said chosen halogenated alkylsilane compound comprises chlorodimethylsilane.

6. The method of claim 4 wherein:
   (1) in Formula I, the silicon-containing radical is attached to the aromatic ring in the para position;
   (2) in step "a" said chosen silylating agent comprises n-butyllithium and chlorotrimethyl silane; and
   (3) in step "b" said chosen halogenated alkylsilane compound comprises chlorodimethylsilane.

7. A compound having Formula III

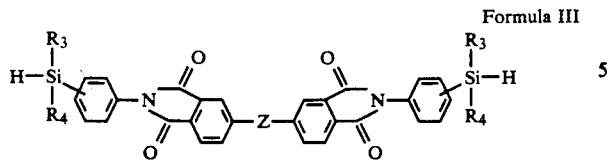

Formula III where $R_3$ and $R_4$ are each selected from the group consisting of a $C_1$ to $C_6$ alkyl group and an aryl group, and Z is a divalent radical selected from the group consisting of $-C(CF_3)_2-$, CO, $SO_2$, and O.

8. The compound of claim 7 wherein:
   (a) the silicon-containing radical is attached to the aromatic ring in the para position;
   (b) $R_3$ and $R_4$ are each methyl; and
   (c) Z is 13 $C(CF_3)_2-$.

9. The compound of claim 7 wherein:
   (a) the silicon-containing radical is attached to the aromatic ring in the meta position;
   (b) $R_3$ and $R_4$ are each methyl; and
   (c) Z is $-C(CF_3)_2-$.

10. A method for forming a compound having Formula III

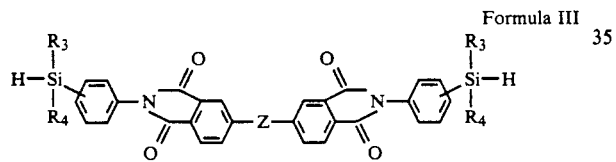

Formula III where $R_3$ and $R_4$ are each selected from the group consisting of a $C_1$ to $C_6$ alkyl group and an aryl group, and Z is a divalent radical selected from the group consisting of $-C(CF_3)_2$, CO, $SO_2$, and O comprising the steps of:

(a) reacting a bromoaniline compound with a chosen silylating agent to form a compound having the formula

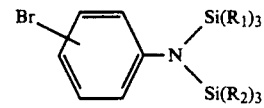

where $R_1$ and $R_2$ are each a $C_1$ to $C_4$ alkyl group, or where the group $-NSi(R_1)_3Si(R_2)_3$ is 2,2,5,5-tetramethyl-1-aza-2,5disilacyclopentane (b) reacting the compound formed in step "a" with n-butyllithium, followed by reaction with a chosen halogenated silane compound to form a compound having Formula II;

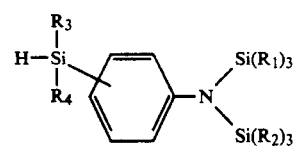

Formula II where $R_1$, $R_2$, $R_3$, and $R_4$ are as defined above.

(c) reacting the compound of Formula II formed in step "b" with a dianhydride compound having the formula

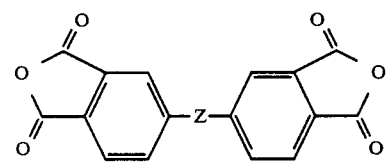

where Z is as defined above to form the compound having Formula III.

11. The method of claim 10 wherein:
   (1) in Formula I, the silicon-containing radical is attached to the aromatic ring in the meta position,
   (2) in step "a" said chosen silylating agent comprises 1,1,4,4-tetramethyl-1,4-bis(N,N-diethylamino)-1,4-disilabutane; and
   (3) in step "b" said chosen halogenated alkylsilane compound comprises chlorodimethylsilane.

12. The method of claim 10 wherein:
   (1) in Formula I, the silicon-containing radical is attached to the aromatic ring in the para position,
   (2) in step "a" said chosen silylating agent comprises n-butyllithium and chlorotrimethylsilane; and
   (3) in step "b" said chosen halogenated alkylsilane compound comprises chlorodimethylsilane.

* * * * *